United States Patent

Carra et al.

[11] Patent Number: 5,126,498
[45] Date of Patent: * Jun. 30, 1992

[54] PROCESS FOR THE SEPARATION OF ISOMERIC DICHLOROTOLUENES

[75] Inventors: Sergio Carra, Milan; Renato Paludetto, Pioltello; Guiseppe Storti; Massimo Morbidelli, both of Milan, all of Italy; Bernard Gurtner, Grenoble; Raymond Commandeur, Vizille, both of France

[73] Assignee: Atochem, Courbevoie, France

[*] Notice: The portion of the term of this patent subsequent to Aug. 23, 2005 has been disclaimed.

[21] Appl. No.: 613,459

[22] Filed: Nov. 9, 1990

Related U.S. Application Data

[63] Continuation of Ser. No. 791,364, Oct. 25, 1985, abandoned.

Foreign Application Priority Data

Oct. 26, 1984 [FR] France ................................. 8416406

[51] Int. Cl.$^5$ ............................................ C07C 17/38
[52] U.S. Cl. ...................................................... 570/211
[58] Field of Search .......................................... 570/211

[56] References Cited

U.S. PATENT DOCUMENTS 2,958,708 11/1960 Fleck et al. .......................... 570/211
4,254,062 3/1981 Wambach et al. .................. 570/211
4,371,721 2/1983 Wu ...................................... 570/211
4,766,262 8/1988 Carra et al. ......................... 570/211

FOREIGN PATENT DOCUMENTS 125077 11/1984 Japan ................................. 570/211

OTHER PUBLICATIONS

"Zeulite Chemistry and Catalysis", p. 297, Adsorption Applications, Rabo, Editor 1976.

Primary Examiner—Marianne Cintins
Assistant Examiner—Kimberly J. Kestler

[57] ABSTRACT

The process for the separation of isomeric dichlorotoluenes, comprising the steps of:
  (a) passing a mixture containing isomeric dichlorotoluenes over a zeolite of the ZSM5 type having the composition (expressed in molar ratios) of $(0.9+0.2)$ $M_{2/n}O:Al_2O_3$: $(10-100)$ $SiO_2$: z $H_2O$ in which M is at least one cation selected from H, an alkali metal, an alkaline earth metal or a tetraalkylammonium cation; n is the valency of M; and z is between 0 and 40:
  (b) separating the non-adsorbed dichlorotoluenes;
  (c) contacting the zeolite containing the adsorbed isomers with an eluent; and
  (d) separating the isomers from the eluent.

6 Claims, No Drawings

PROCESS FOR THE SEPARATION OF ISOMERIC DICHLOROTOLUENES

This application continuation of application Ser. No. 791,364, filed Oct. 25, 1985, now abandoned.

BACKGROUND OF THE INVENTION

The invention relates to a process for the separation of isomeric dichlorotoluenes by absorption on zeolites. Dichlorotoluenes are generally prepared by chlorination of toluene or of monochlorotoluenes in the presence of a Lewis acid such as the trichlorides in the presence of a Lewis acid such as the trichlorides of aluminum, iron or antimony, by themselves or together with a cocatalyst such as, for example, sulphur or sulphur chlorides.

The chlorination reaction leads to mixtures containing the 2,4-, 2,5-, 2,6-, 3,4- and 2,3-dichlorotoluenes. These mixtures can be separated by distillation of the other chlorination products of toluene or of the monochlorotoluenes (monochlorotoluene and trichlorotoluenes). The five isomers mentioned above are obtained in varying proporations depending on the starting products used for the chlorination reaction.

It is also possible to separate the mixtures of dichlorotoluenes by distillation into two fractions boiling at about 201° C. and about 209° C. The first fraction comprises the 2,6-, 2,4-, and 2,5-isomers and the second fraction is composed of the 3,4- and 2,3- isomers.

It is generally accepted that it is not possible to obtain all the various isomers in a pure state under economically acceptable conditions by conventional techniques of distillation or of fractional crystallization. In particular, distillation does not allow the separation of the constituents of the two fractions boiling at 201 and 209° C. approximately, because of the very slight differences in boiling point of the isomers. Only 2,3-dichlorotoluene can be separated off by distillation, provided that o-chlorotoluene is used as the starting material. As regards fractional crystallization, it can generally not be used because numerous eutectic mixtures exist.

In view of these considerations, other separation techniques have been proposed. In particular, U.S. Pat. No. 4,254,062 describes a process for the separation of isomeric dichlorotoluenes which employs zeolites of types X or Y.

SUMMARY OF THE INVENTION

The invention proposes a new process for the separation of the isomeric dichlorotoluenes.

Briefly, the invention comprises the process of separating isomeric dichlorotoluenes comprising (a) passing a mixture containing isomeric dichlorotoluenes over zeolite of the ZSM5 type, having the following composition (expressed in molar ratios $(0.09+0.2$ $M_{2/n}O$ : $Al_2O_3$ : $(10-100)$ $SiO_2$:$z$ $H_2O$ in which M is at least one cation selected from H, an alkali metal, an alkaline earth metal, or a tetraalkylammonium cation: n is the valency of M; and z is between O and 40; (b) separating the non-absorbed dichlorotoluenes; (c) contacting the zeolite containing the absorbed isomers with an eluent; and (d) separating the isomers from the eluent.

DETAILED DESCRIPTION

In the formula given above for the zeolite of the ZSM5 type, the symbol M preferably represents potassium, sodium or hydrogen. However, and as long as the value 0.9 +0.2 is adhered to, the symbol M can represent more than one cation. Very particularly, there may be mentioned the combinations of the sodium cation with one or more monovalent or divalent cations such as potassium, barium, calcium or strontium. M may also wholly or partly consist of one or more tetraalkylammonium cations, with the alkyl groups preferably containing from 2 to 5 carbon atoms.

The ZSM5 zeolites which can be used in the process according to the invention, their processes of preparation and their X-ray diffraction diagrams are described in French Patent 1,587,860, of which the contents are incorporated herein by reference.

Amongst these ZSM5 zeolites there may very especially be recommended the zeolites of the formula (expressed in molar ratios)

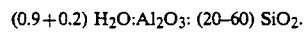

$(0.9+0.2)$ $H_2O:Al_2O_3$: $(20-60)$ $SiO_2$.

The process according to the invention can be carried out in a liquid phase or in the vapor phase. This adsorption-desorption process can be carried out at between about 25° and 350° C. and preferably between 100° and 300° C., and over a large range of pressure (for example, the pressure can range from about 1 bar to about 30 bars).

The mixture of the isomeric dichlorotoluenes can be brought into contact with the zeolite in a conventional apparatus for adsorption separation. In particular, apparatus permitting continuous or discontinuous operations may be used. The shape and dimensions of the said apparatus can be optimized by a man skilled in this art and do not per se form a subject of the present invention.

In general, the zeolite employed in the adsorption-desorption apparatus, for example in an adsorption column, is in the form of particles whose size can be between 0.1 and 10mm and preferably between 0.5 and 3mm.

The above mentioned zeolite is brought into contact with the mixture of isomeric dichlorotoluenes. Though the adsorption capacity of this type of zeolite towards the five above mentioned isomers makes it possible per se to effect a separation starting from the five isomers, it is only possible to pass over the zeolite a mixture which only contains some of these isomers: thus it is possible, after having separated the 2,3- and 3,4-isomers, (which boil at about 209° C.) by distillation from the 2,4- 2,5- and 2,6-isomers (which boil at about 201° C.), only to subject the above mentioned fractions to the adsorption-desorption process, since the zeolite ZSM5 differently adsorbs the 3,4- and 2,3-isomer, in the one case, and the 2,4-, 2,5- and 2,6-isomers, in the other case. Of course, mixtures in which at least one of the above mentioned isomers has beforehand been concentrated can be treated by the process according to the invention.

The total or partial mixture of isomers, as specified above, is partially adsorbed on the zeolite. The non-adsorbed dichlorotoluenes can be collected at the outlet of the adsorption-desorption apparatus. The zeolite is then brought into contact with an eluent, that is to say a compound which allows the isomers to be displaced and hence to be separated. Preferably, a compound whose activity toward the zeolite is of the some order as that o the dichlorotoluenes concerned is chosen. By way of illustration of eluents which can be used in the process according to the invention there may be mentioned especially hydrogen, nitrogen, oxygen, carbon dioxide, helium, hydrocarbons, and especially alkanes such as methene, ethane, propane, n-hexane, n-heptane an n-octane, cycloalkanes, especially cyclolhexane, monocyclic or polycyclic aromatic compounds which are optionally substituted and/or halogenated, such as benzene,toluene, ethylbenzene, cumene tetrahydronaphthalene, decahydronaphthalene, monochloro-toluenes and dichlorotoluenes, and also polar compounds such as water or ammonia.

Preferably cyclohexane, toluene, ethylbenzene, tetrahydronaphthalene is used in the invention.

After a treatment with the desorbing agents or eluents, the isomers can themselves be separated from the said agents by using conventional methods, for example distillation.

The process according to the invention makes it possible, in general terms, to modify the composition of mixtures containing the five isomeric dichlorotoluenes, because of the remarkable selectivity of the ZSM5 zeolite. This selectivity is defined by the fraction:

$$\frac{\text{molar fraction of isomer (i) in the desorbate}}{\text{molar fraction of isomer (j) in the desorbate}} \bigg/ \frac{\text{molar fraction of (i) in the initial mixture}}{\text{molar fraction of (j) in the initial mixture}}$$

This process very particularly makes it possible to separate into their constituents the two fractions respectively boiling a 201° C. and 209° C. and in the case of the fraction boiling at 201° C. and consisting of the 2,4- 2,5- and 2,6-isomers it allows the 2,6-isomer to be obtained very efficiently.

The examples which follow illustrate the invention. In the examples, the zeolite used was either a ZSM5 zeolite or the mean molar formula (0.9+0.2) H₂O: Al₂O₃:(30–40) SiO₂ 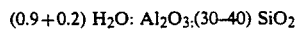

in the form of particles of size 0.5 to 2mm (Examples 1 to 27) or a zeolite in which a part of the hydrogen ions have been replaced by potassium ions. This zeolite is prepared by impregnating the zeolite defined above with an aqueous potassium chloride solution (60 g/l). The treatment is carried out at 90° C. for 3 hours and is followed by washing with water for 1 hour, the set of operations being repeated 3 times. The zeolite is dried for 10 hours and is then heated, before use, for 1 hour at 400–500° C. under a nitrogen atmosphere (Example 28).

The mixture of isomeric dichlorotoluenes used consists either of the industrial product obtained by chlorination of toluene (Example 1), or consists of fractions of the said industrial product, boiling at about 209° C. and about 201° C. (Examples 2 and 3) or consists of binary compositions in which the proportions of the constituents have been varied (Examples 4 and subsequent examples).

The experiments are carried out in a column of 1 cm diamete and 1 m height, containing 10 g of zeolite. Before the experiments, nitrogen at 450° C. is passed over the zeolite for 16 hours and the zeolite is then saturated with ethylbenzene. The adsorption temperature is 220° C. 10 cm³ of the mixture of isomeric dichlorotoluenes are introduced into the column at a rate of 0.5 cm³/ minute.

Thereafter 15 cm³ of ethylbenzene are passed into the column at the same rate of 0.5 cm³/ minute. The solution of isomeric dichlorotoluenes in ethylbenzene is collected and the molar composition of the desorbate is determined.

EXAMPLE 1

The process described above is applied to an industrial of isomeric dichlorotoluenes. In the table which follows, the abbreviations have the following meanings:

dct isomer: dichlorotoluene isomer entry mole %: molar fraction of the isomer concerned in the composition subjected to adsorption/desorption exit mole %: molar fraction of the isomer concerned in the desorbate.

selectivity/2,6-: selectivity for the isomer concerned relative to the 2,6-isomer.

The selectivity is only given with reference to the 2,6-isomer so as not to overload the table, but of course the relative selectivity for any 2 isomers can easily be calculated, employing the equation given earlier.

| dct isomer | Entry mole % | Exit mole % | Selectivity |
|---|---|---|---|
| 2,5– | 36.5 | 37.2 | 1.721 |
| 2,6– | 8.5 | 5.0 | 1.0 |
| 2,4– | 34.0 | 38.1 | 1.90 |
| 3,4– | 13.0 | 14.2 | 1.84 |
| 2,3– | 8.0 | 5.6 | 1.7 |

EXAMPLE 2

The process is applied to the mixture of 2,3- and 3,4-isomers boiling at about 209° C. (a fraction of the industrial product).

The following are found:

| Initial composition (mole %) | | Composition of the desorbate (mole %) | | Selectivity |
|---|---|---|---|---|
| 2,3– | 3,4– | 2,3– | 3,4– | 2,3–/3,4– |
| 49.7 | 50.3 | 37.9 | 62.1 | 1.615 |

EXAMPLES 3 to 7

The process described above is applied to the fraction boiling at 201° C. (a fraction of the industrial product).

| | Initial composition (mole %) | | | Composition of desorbate (mole %) | | | Selectivity 2,4–/2,6– 2,5–/2,6– 2,4–/2,5– | | |
|---|---|---|---|---|---|---|---|---|---|
| Example | 2,5– | 2,6– | 2,4– | 2,5– | 2,6– | 2,4– | | | |
| 3 | 21.2 | 58.4 | 20.4 | 30.3 | 36.5 | 33.2 | 2.61 | 2.29 | 1.14 |
| 4 | 39.9 | 39.7 | 20.3 | 51.9 | 20.4 | 27.7 | 2.65 | 2.53 | 1.05 |
| 5 | 23.0 | 39.9 | 37.4 | 29.5 | 20.9 | 49.6 | 2.53 | 2.44 | 1.04 |
| 6 | 38.8 | 19.4 | 41.8 | 40.4 | 11.4 | 48.2 | 1.97 | 1.77 | 1.11 |
| 7 | 21.1 | 19.4 | 59.5 | 20.2 | 10.7 | 69.1 | 2.11 | 2.17 | 0.97 |

EXAMPLES 8 to 10

The process described above is applied to compositions containing 2 or 3 isomers of the fraction boiling at 201° C.

| Example | Initial composition (mole %) 2,6— | 2,5— | 2,4— | Composition of the desorbate (mole %) 2,6— | 2,5— | 2,4— | Selectivity (S) |
|---|---|---|---|---|---|---|---|
| 8 | — | 50.1 | 49.9 | — | 6.8 | 53.2 | $S_{2,4-}/_{2,5-} = 1.14$ |
| 9 | 49.3 | 50.7 | — | 27.5 | 72.5 | — | $S_{2,5-}/_{2,6-} = 2.56$ |
| 10 | 50.3 | — | 49.7 | 26.3 | — | 73.7 | $S_{2,4-}/_{2,6-} = 2.83$ |

EXAMPLES 11 to 19

The process is applied to mixtures of the 2,4- and 2,6-isomers in varying proportions.

| Example | Initial composition (mole %) 2,4— | 2,6— | Composition of desorbate (mole %) 2,4— | 2,6— | Selectivity 2,4—/2,6— |
|---|---|---|---|---|---|
| 11 | 10.8 | 89.2 | 50.5 | 49.5 | 8.40 |
| 12 | 19.0 | 81.0 | 51.6 | 48.4 | 4.55 |
| 13 | 24.7 | 75.3 | 58.6 | 41.4 | 4.32 |
| 14 | 40.2 | 59.8 | 68.7 | 31.3 | 3.27 |
| 15 | 48.7 | 51.3 | 71.9 | 28.1 | 2.70 |
| 16 | 59.6 | 40.4 | 81.5 | 19.5 | 2.98 |
| 17 | 75.0 | 25.0 | 86.3 | 13.7 | 2.10 |
| 18 | 79.8 | 20.2 | 89.8 | 10.2 | 2.23 |
| 19 | 89.4 | 10.6 | 93.3 | 6.7 | 1.59 |

EXAMPLES 20 to 25

The process is applied to mixtures of the 2,5- and 2,6-isomers in varying proportions.

| Example | Initial composition (mole %) 2,5— | 2,6— | Composition of the desorbate (mole %) 2,5— | 2,6— | Selectivity 2,5—/2,5— |
|---|---|---|---|---|---|
| 20 | 9.3 | 90.7 | 35.0 | 65.8 | 5.26 |
| 21 | 10.0 | 90.0 | 31.2 | 68.8 | 4.09 |
| 22 | 29.7 | 70.3 | 35.1 | 67.9 | 2.60 |
| 23 | 48.8 | 51.2 | 67.2 | 32.8 | 2.15 |
| 24 | 69.9 | 30.1 | 82.8 | 17.2 | 2.09 |
| 25 | 87.4 | 12.6 | 93.2 | 6.8 | 2.00 |

EXAMPLES 26 and 27

The experiment on the separation of mixtures of the 2,4-, 2,5- and 2,6-isomers is repeated in the liquid phase, in solution in decahydronaphthalene, at 25 and 90° C.

| Example | Isomers | % of Isomer in the solution initial at 25° C. | final at 90° C. | Relative % of the two isomers initial at 25° C. | | final at 90° C. | |
|---|---|---|---|---|---|---|---|
| 26 | 2,6— | 10.06 | 10.04 | 9.75 | 50 | 53 | 55.3 |
|  | and 2,4— | 10.06 | 8.94 | 7.89 | 50 | 47 | 44.7 |
|  | 2,6— | 10.05 | 10.25 | 9.70 | 50 | 58.7 | 58.6 |
|  | and 2,5— | 10.05 | 7.22 | 6.85 | 50 | 41.3 | 41.4 |

It emerges from this table that the absolute percentage of a 2,6-isomer in the final solution is substantially identical to the starting percentage, while the reduction in concentration of the 2,4- and 2,5-isomers is evident. Accordingly, there is also a high selectivity in the liquid phase.

EXAMPLE 28

The zeolite containing potassium cations, the preparation of which has been described above, is used.

On applying the technique of measurement mentioned earlier to the experiments carried out on the industrial mixture of Example 1, the following relative selectivities of the isomers are observed:

| Zeolite | SELECTIVITY 2,4—/2,6— | 2,5—/2,6— | 2,4—/2,5— | 3,4—/2,3— |
|---|---|---|---|---|
| Cation K | 1.74 | 1.40 | 1.25 | 1.44 |
| Example 1 | 1.90 (reminder) | 1.72 (reminder) | 1.10 | 1.57 |

EXAMPLES 29 to 31 (comparative examples)

The process is applied to binary mixtures of 2,4- 2,5- and 2,6-isomers, using a hu Yk zeolite, that is to say a Y zeolite in which the cations are potassium cations.

The following results are observed:

| Example | Initial composition (mole %) 2,6— | 2,5— | 2,4— | Composition of the desorbate (mole %) 2,6— | 2,5— | 2,4— | Selectivity |
|---|---|---|---|---|---|---|---|
| 29 | — | 50.3 | 49.7 | — | 42.9 | 57.1 | $2,4-/2,5- = 1.35$ |
| 30 | 49.5 | 50.5 | — | 49.3 | 50.7 | — | $2,5-/2,6- = 1.05$ |
| 31 | 50.9 | — | 49.1 | 42.5 | — | 57.5 | $2,4-/2,6- = 1.29$ |

It is found, by comparison with the results of Examples 8 to 10 (substantially equimolecular starting mixtures) that while the 2,4-/2,5- selectivity is of the same order of magnitude, the 2,5-/2, selectivities, on the other hand, are substantially improved with the zeolites of the process of the invention.

While the invention has been described in connection with a preferred embodiment, it is not intended to limit the scope of the invention to a particular form set forth, but, on the contrary, it is intended to cover such alternatives, modifications and equivalents as may be included within the spirit and scope of the invention as defined by the appended claims.

What is claimed:

1. The process for the separation of isomeric dichlorotoluene comprising the steps of:
   (a) passing a mixture containing isomeric dichlorotoluene over a zeolite of the ZSM5 type having the composition (expressed in molar ratios) of $(0.9 + 0.2) M_2/nO:Al_2O_3:(10-100) SiO_2:z H_2O$ in which M is H, n is the valency of M; and z is between 0 and 40:
   (b) separating the non-adsorbed dichlorotoluenes;
   (c) contacting the zeolite containing the adsorbed isomers with an eluent; and
   (d) separating the isomers from the eluent.

2. The process of claim 1, wherein the zeolite is of the formula (in molar rations):

$(0.9+0.2) H_2O:Al_2O_3:(20-60) SiO_2$.

3. The process of claim 1, wherein the mixture of isomeric dichlorotoluenes is brought into contact with the zeolite in a liquid or gaseous phase at a temperature between about 25° to 350° C. and under a pressure of between about 1 bar to 30 bars.

4. The process of claim 1, wherein the mixture brought into contact with the zeolite is selected from a mixture consisting of 2,3- 3,4-dichlorotoluene, a mixture consisting essentially of 2,4-, 2,5-, or 2,6-dichlorotoluene, or a mixture comprising 2,3-, 3,4-, 2,4- 2,5- and 2,6-dichlorotoluene.

5. The process of claim 1, wherein the mixture brought into contact with the zeolite is concentrated beforehand in respect of at least one of its constituents.

6. The process according to claim 1, wherein the eluent is hydrogen, nitrogen, oxygen, carbon dioxide, helium, methane, ethane, propane, n-hexane and n-heptane n-octane, cyclohexane, benzene, toluene, ethylbenzene, cumene, tetrahydronaphthalene, decahydronaphthalene, monochlorotoluene, dichlorotoluene, water or ammonia.

* * * * *

UNITED STATES PATENT AND TRADEMARK OFFICE
CERTIFICATE OF CORRECTION

PATENT NO. : 5,126,498
DATED : June 30, 1992
INVENTOR(S) : Carra, et al

It is certified that error appears in the above-indentified patent and that said Letters Patent is hereby corrected as shown below:

On the title page, under Other Publication change "Zeulite" to --Zeolite--.

Col. 1, lines 13 and 14, cancel the phrase "such as the trichlorides in the presence of a Lewis acid".

Col. 1, line 24, correct "proporations" to read "proportions".

Col. 1, line 56, cancel "0.09" and substitute therefor -- 0.9 --.

Col. 2, line 45, cancel "only" and substitute therefor -- also --.

Col. 2, line 65, cancel "some" and substitute therefor -- same --.

Col. 3, line 3, cancel "methene" and substitute therefor -- methane --.

UNITED STATES PATENT AND TRADEMARK OFFICE
CERTIFICATE OF CORRECTION

PATENT NO. : 5,126,498
DATED : June 30, 1992
INVENTOR(S) : Carra, et al

It is certified that error appears in the above-indentified patent and that said Letters Patent is hereby corrected as shown below:

Col. 4, under the column in line 24 headed "dct isomer", amend the second entry "2.6" to read "2,6".

Col. 5, line 6, amend "2.6" to read -- 2,6 --.

Col. 7, Claim 4, line 3, cancel "2,3-3,4" and substitute therefor -- 2,3 and 3,4 --.

Signed and Sealed this

Twenty-eighth Day of December, 1993

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,126,498
DATED : June 30, 1992
INVENTOR(S) : Carra, et al

It is certified that error appears in the above-indentified patent and that said Letters Patent is hereby corrected as shown below:

Col. 1, lines 13 and 14, cancel the phrase "such as the trichlorides in the presence of a Lewis acid".

Col. 1, line 24, correct "proporations" to read "proportions".

Col. 1, line 56, cancel "0.09" and substitute therefor -- 0.9 --.

Col. 2, line 45, cancel "only" and substitute therefor -- also --.

Col. 2, line 65, cancel "some" and substitute therefor -- same --.

Col. 3, line 3, cancel "methene" and substitute therefor -- methane --.

Signed and Sealed this

Eighth Day of November, 1994

Attest:

BRUCE LEHMAN

Attesting Officer

Commissioner of Patents and Trademarks